United States Patent
Bombardelli et al.

(10) Patent No.: US 7,887,855 B2
(45) Date of Patent: Feb. 15, 2011

(54) **FORMULATIONS CONTAINING *CYNARA SCOLYMUS* AND *PHASEOLUS VULGARIS* EXTRACTS WHICH ARE USEFUL IN THE TREATMENT OF OBESITY**

(75) Inventors: Ezio Bombardelli, Groppello Cairoli (IT); Gabriele Fontana, Milan (IT); Andrea Giori, Milan (IT); Paolo Morazzoni, Milan (IT); Cesare Ponzone, Milan (IT); Massimo Ronchi, Milan (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 12/529,990

(22) PCT Filed: Mar. 6, 2008

(86) PCT No.: PCT/EP2008/001787
§ 371 (c)(1),
(2), (4) Date: Sep. 4, 2009

(87) PCT Pub. No.: WO2008/107184
PCT Pub. Date: Sep. 12, 2008

(65) Prior Publication Data
US 2010/0136145 A1  Jun. 3, 2010

Related U.S. Application Data

(60) Provisional application No. 60/905,320, filed on Mar. 7, 2007.

(30) Foreign Application Priority Data
Mar. 7, 2007  (EP) .................................. 07425132

(51) Int. Cl.
*A01N 65/00* (2009.01)

(52) U.S. Cl. .................................................... 424/725

(58) Field of Classification Search ....................... None
See application file for complete search history.

(56) References Cited

U.S. PATENT DOCUMENTS

| 4,826,877 A | 5/1989 | Stewart et al. |
| 6,818,234 B1 | 11/2004 | Nair et al. |

FOREIGN PATENT DOCUMENTS

| WO | 2007/006391 | 1/2007 |
| WO | 2007/071334 | 6/2007 |

OTHER PUBLICATIONS

P. Nazni et al., "Hypoglycemic and Hypolipidemic Effect of *Cynara scolymus* among Selected Type 2 Diabetic individuals", Pakistan Journal of Nutrition 2006 Pakistan, vol. 5, No. 2, 2006, XP009086811, ISSN: 1680-5194, pp. 147-151.
Leonardo Celleno et al., "A dietary Supplement Containing Standardized *Phaseolus vulgaris* Extract Influences Body Composition of Overweight Men and Women", International Journal of Medical Sciences, Jan. 26, 2007, XP002442835, ISSN:1449-1907, pp. 45-52.
M. A. Tormo et al., "Hypoglycaemic and anorexigenic activities of an alpha-amylase inhibitor from white kidney beans (*Phaseolus vulgaris*) in Wistar rats", British Journal of Nutrition, Cambridge University Press, Cambridge, GB, vol. 92, No. 5, Nov. 2004, ISSN: 0007-1145, pp. 785-790.
International Search Report dated Jun. 9, 2008, from corresponding PCT application.

*Primary Examiner*—Michael V Meller
(74) *Attorney, Agent, or Firm*—Young & Thompson

(57) ABSTRACT

The present invention relates to a *Cynara scolymus* extract with a high content of caffeoylquinic acids, and a composition containing said *Cynara scolymus* extract with a *Phaseolus vulgaris* extract. Said composition is useful in reducing obesity as it reduces cholesterol, triglycerides and blood glucose by sensitizing the cells to insulin. This combination, when taken before meals, reduces the appetite, leading to a reduction in body weight. The extracts are preferably formulated in *Oenothera biennis* oil, fish oil, or oils rich in unsaturated ω-3 fatty acids.

1 Claim, No Drawings

FORMULATIONS CONTAINING CYNARA SCOLYMUS AND PHASEOLUS VULGARIS EXTRACTS WHICH ARE USEFUL IN THE TREATMENT OF OBESITY

FIELD OF INVENTION

The present invention relates to formulations containing an extract of *Cynara scolymus*, preferably with a high content of caffeoylquinic acids, and an extract of *Phaseolus vulgaris*, in a ratio between 1:0.25 and 1:1.

This composition is useful in reducing obesity because it reduces cholesterol, triglycerides, blood glucose and the appetite.

BACKGROUND OF THE INVENTION

Obesity is currently one of the major health problems, especially in the industrialised countries, with serious consequences in cardiocirculatory and skeletal terms.

Carbohydrates are an important source of calories, and contribute to the synthesis of fats in individuals predisposed to obesity or type II diabetes. As hyperglycaemia leads to an increase in energy deposits, the availability of substances that reduce bioavailable glucose is very important. As starches are the main source of glucose, specific α-glucosidase and α-amylase inhibitors, obtained from plant materials or by synthesis, have been studied. It has long been known that some seeds and pulses contain substances which can have adverse effects on the diet if eaten before they are completely cooked. Many pulses contain protease inhibitors, amylase inhibitors and substances that discourage predators from continuing to use them by reducing the appetite. These substances, called phytohaemagglutinins, can cause hyperplasia of the pancreas at high doses, but can be useful in appetite control at lower doses.

At high doses, these lectins survive the intestinal transit and bond to the enterocytes where they cause the secretion of cholecystokinin, a trophic hormone that stimulates secretion by the pancreas, consequently causing its enlargement. Cholecystokinin also has favourable effects, because it reduces the appetite by reducing gastric motility.

It is known from the literature that aqueous or hydroalcoholic extracts of *Cynara scolymus* have hypocholesterolaemic, choleretic and antidyspeptic activity. The hypocholesterolaemic activity, which has been reported for many years, is associated with two classes of substances: cynarin, a dicaffeoylquinic acid, and flavonoids deriving from luteolin, which have been demonstrated in vitro to inhibit cholesterol synthesis in the liver. Part of the activity is associated with the choleretic action specific to *Cynara scolymus* extracts. A process of extraction of *Cynara scolymus* is described in WO 2007/006391.

DESCRIPTION OF THE INVENTION

It has now been found that by combining *Cynara scolymus* extracts with *Phaseolus vulgaris* extracts, surprising effects on the reduction of body weight are obtained, proportional to the dose administered; the data in rats suggested that the effect on body weight reduction is not simply associated with a reduction in the blood glucose level, but also with a definite reduction in food consumption. Various pharmacological experiments demonstrate that this reduced food intake, despite unrestricted access to food, is associated not with a simply toxic effect, but with a modification in the desire to eat.

The combination of an artichoke extract, which helps to increase the elimination of fats and glucose by modifying glucose transport in the intestine and liver, with substances that reduce the metabolism of starch, is particularly important in the maintenance of body weight, and blocks its progress.

DETAILED DESCRIPTION OF THE INVENTION

The extracts which can be used according to this invention are commercial artichoke extracts, extracts according to WO 2007/006391, or an artichoke extract with a high content of caffeoylquinic acids and luteolin glycosides, obtainable by extraction from undried edible heads with C1-C3 alcohols or mixtures thereof with water.

The extraction from the undried edible heads of *Cynara scolymus* is preferably performed with ethanol or ethanol/water mixtures, especially ethanol/water in the ratio of 7:3 v/v. After purification, an extract is obtained which differs from known extracts due to its high content of caffeoylquinic acids and flavonoids expressed as luteolin glycosides. The extract also possesses hypoglycaemic activity. The extract can be prepared from various globe artichoke cultivars, preferably from the spiny variety, and even more preferably from the Sardinian spiny variety.

The preferred artichoke extract has a caffeoylquinic acid content ranging between 30 and 60%, preferably around 45%, and a flavonoid content, expressed as luteolin glycosides, ranging between 2 and 5%, preferably around 2.5%.

A commercial extract can be used as *Phaseolus vulgaris* extract; however, the *Phaseolus vulgaris* extract described in PCT/EP2006/012012 is preferred. Said extract is obtainable by extraction from *Phaseolus* sp. with mixtures of ethanol and water, and is characterised by an alpha-amylase inhibitor content of between 1200 and 1600 USP/mg (HPLC titre between 7 and 14% w/w) and a phytohaemagglutinin content of between 12,000 and 30,000 HAU/g. Said extract can be obtained by a process which comprises:

a) extraction of *Phaseolus* sp. with aqueous buffers having a pH ranging between 3 and 6.5 and subsequent separation of the extract from the biomass, which can possibly be further extracted with the buffer until exhaustion in alpha-amylase and phytohaemagglutinin inhibitors;

b) filtration or centrifugation of the combined extracts and concentration to a volume corresponding to approx. 10% of the weight of the biomass of the starting extract after centrifugation;

c) differential precipitation of the concentrated aqueous extract with diluted ethanol, to a final concentration between 60 and 70% v/v;

d) separation of precipitate and reprecipitation from demineralised water with 60% ethanol or diafiltration on a membrane with a 10,000 Da cut-off, and drying of precipitation residue.

The combination of the two extracts in a ratio between 1:0.25 and 1:1 comprises doses ranging from 50 to 500 mg per dose for the *Cynara scolymus* extract, preferably 200 mg, and from 50 to 200 mg per dose for the *Phaseolus vulgaris* extract, preferably 100 mg, to be taken before meals or whenever foods rich in carbohydrates are eaten.

The hypoglycaemic activity of the composition according to the invention is surprisingly superior to the hypoglycaemic activity of the two constituents alone. The results, obtained according to the method described by Tormo M A et al., Br. J. Nutr. 96, 539, 2006, are set out in the Table.

TABLE

Effect of purified Artichoke extract, *Phaseolus vulgaris* extract and their combination on glycemia in Wistar rats given a restricted amount of food with a 1 hour/day limited access.

| Purified artichoke extract mg/kg p.o. | *Phaseolus vulgaris* extract mg/kg p.o. | AUC of plasma glucose levels (mg/dL) |
|---|---|---|
| 0 | 0 | 30800 ± 950 |
| 50 | 0 | 25100 ± 700* (−18%) |
| 0 | 50 | 27700 ± 600 (−10%) |
| 25 | 25 | 19800 ± 800** (−36%) |

Number of animals/group: 8
*p < 0.05
**p < 0.01 vs controls

The composition according to the invention is suitable to be incorporated in pharmaceutical formulations such as tablets, dragrées, soft and hard gelatin capsules and cellulose capsules. The extracts are preferably formulated in oils rich in polyunsaturated ω3/ω6 acids such as *Oenothera biennis* (evening primrose) oil.

The same results as observed in laboratory animals have been confirmed in humans at doses of between 50 and 1000 mg a day.

The following examples illustrate the invention in detail.

EXAMPLE 1

Preparation of Extract of *Cynara scolymus* vr. *Spinosus*

Load 2 kg of *Cynara scolymus* heads, vr. *Sardinian spinosus*, chopped and frozen at the time of harvesting, into a percolator with a heating jacket, and cover with 4760 ml of 95° EtOH to obtain an alcohol content of approx. 70% (assuming an 85% water content in the plant). Maintain in contact for 3 hours at 70° C., then unload. In the successive extractions, extract with EtOH 70% v/v at 70° C., covering the plant, with a minimum contact time of 3 hours. Perform a total of 5 extractions, using approx. 15 l of solvent.

Combine the percolates and concentrate under vacuum at 35° C. to approx. 15% of dried residue.

Leave to cool at ambient temperature, separate the insoluble fraction, and load the clear aqueous solution into a column packed with 530 ml of XAD-7 HP resin.

Wash the column, first with 530 ml of water (eliminating the eluate) and then with 1325 ml of 90% EtOH. Concentrate the hydroethanolic eluate and dry at 50° C. under vacuum for 24 hours. 18.59 g of purified extract will be obtained. HPLC titres: caffeoylquinic acids 49.13%, flavonoids 2.68%.

EXAMPLE 2

Formulation of *Cynara scolymus* and *Phaseolus vulgaris* Extracts into Oily Suspension for Soft Gelatin Capsules Unit Composition:

| | |
|---|---|
| *Cynara scolymus* extract | 100 mg |
| *Phaseolus vulgaris* extract | 100 mg |
| Glyceryl monostearate | 30 mg |
| Soya lecithin | 10 mg |
| *Oenothera biennis* oil q.s. for | 700 mg |

Manufacturing Process
Heat *Oenothera biennis* oil to approx. 70° C. and melt the glyceryl monostearate in it under agitation.
Add the soya lecithin to the solution obtained.
Disperse the *Cynara scolymus* and *Phaseolus vulgaris* extracts in the solution obtained, ensuring even distribution.
Gradually cool the solution obtained, keeping it under agitation.

EXAMPLE 3

Formulation of *Cynara scolymus* and *Phaseolus vulgaris* Extracts into Hard Gelatin Capsules Unit composition:

| | |
|---|---|
| *Cynara scolymus* extract | 150 mg |
| *Phaseolus vulgaris* extract | 50 mg |
| Microcrystalline cellulose | 200 mg |
| Lactose | 95 mg |
| Silicon dioxide | 5 mg |

Manufacturing Process
Mix extracts, microcrystalline cellulose, lactose and silicon dioxide.
Divide the mixture obtained between hard gelatin capsules.

EXAMPLE 4

Formulation of *Cynara scolymus* and *Phaseolus vulgaris* Extracts into Modified-release Granules Unit composition:

| | |
|---|---|
| *Cynara scolymus* extract | 100 mg |
| *Phaseolus vulgaris* extract | 50 mg |
| Microcrystalline cellulose | 100 mg |
| Povidone | 10 mg |
| Sodium carboxymethylcellulose | 8 mg |
| Methacrylic acid copolymer | 50 mg |
| Triethyl citrate | 3.2 mg |
| Talc | 8 mg |
| Simeticone | 0.3 mg |

Manufacturing Process
Granulate the extracts, microcrystalline cellulose and sodium carboxymethylcellulose with an aqueous solution of povidone.
Dry and calibrate the granulate obtained.
Coat granules with an aqueous suspension of methacrylic acid copolymer, triethyl citrate, talc and simeticone.

EXAMPLE 5

Formulation of *Cynara scolymus* and *Phaseolus vulgaris* Extracts into Immediate-release Granules Unit Composition:

| | |
|---|---|
| *Cynara scolymus* extract | 100 mg |
| *Phaseolus vulgaris* extract | 50 mg |
| Microcrystalline cellulose | 100 mg |
| Povidone | 10 mg |
| Sodium carboxymethylcellulose | 8 mg |

Manufacturing Process
Granulate the extracts, microcrystalline cellulose and sodium carboxymethylcellulose with an aqueous solution of povidone.
Dry and calibrate the granulate obtained.

EXAMPLE 6

Mixture of *Cynara scolymus* and *Phaseolus vulgaris* Extract Granulates with Different Release Profiles Manufacturing Process Mix 50% of the granulate described in example 4 with 50% of the granulate described in example 5.

Divide the mixture obtained between hard gelatin capsules.

The invention claimed is:

1. A method of reducing obesity or reducing hypoglycemic activity comprising administering a therapeutically effective amount of an extract of *Cynara scolymus* and a therapeutically effective amount of *Phaseolus vulgaris* in a ratio between 1:0.25 and 1:1 (w/w) to a subject in need thereof.

* * * * *

UNITED STATES PATENT AND TRADEMARK OFFICE
CERTIFICATE OF CORRECTION

PATENT NO. : 7,887,855 B2
APPLICATION NO. : 12/529990
DATED : February 15, 2011
INVENTOR(S) : Ezio Bombardelli et al.

Page 1 of 1

It is certified that error appears in the above-identified patent and that said Letters Patent is hereby corrected as shown below:

On column 6, line 2:

"1. A method of reducing obesity or reducing hypoglycemic"

should be replaced with:

--1. A method of reducing obesity or having hypoglycemic--

Signed and Sealed this
Thirty-first Day of May, 2011

David J. Kappos
*Director of the United States Patent and Trademark Office*